United States Patent
Man

(10) Patent No.: US 7,023,951 B2
(45) Date of Patent: Apr. 4, 2006

(54) METHOD AND APPARATUS FOR REDUCTION OF ARTIFACTS IN COMPUTED TOMOGRAPHY IMAGES

(75) Inventor: Bruno De Man, Clifton Park, NY (US)

(73) Assignee: General Electric Company, Niskayuna, NY (US)

(*) Notice: Subject to any disclaimer, the term of this patent is extended or adjusted under 35 U.S.C. 154(b) by 0 days.

(21) Appl. No.: 10/731,062

(22) Filed: Dec. 9, 2003

(65) Prior Publication Data
US 2005/0123089 A1     Jun. 9, 2005

(51) Int. Cl.
*A61B 6/00*     (2006.01)

(52) U.S. Cl. ............................................. 378/8; 378/4
(58) Field of Classification Search ..................... 378/4, 378/7, 8, 901, 6, 15
See application file for complete search history.

(56) References Cited

U.S. PATENT DOCUMENTS

| | | | |
|---|---|---|---|
| 6,125,193 A | | 9/2000 | Han |
| 6,426,988 B1* | | 7/2002 | Yamada et al. ................ 378/4 |
| 6,754,298 B1* | | 6/2004 | Fessler ........................... 378/4 |
| 2001/0028696 A1* | | 10/2001 | Yamada et al. ................ 378/4 |

OTHER PUBLICATIONS

J.F. Williamson, et al, "Prospects for Quantitative Computed Tomography Imaging in the presence of Foreign Metal Bodies using Statistical Image Reconstruction", Med. Phys., vol. 29, No. 10, pp. 2404-2418, Oct. 2002.
G. Wang, et al, "A fast algorithm for metal artifact reduction in X-ray CT", Academic Radiology, pp. 7:607-614, 2000.
B. De. Man, "Iterative Reconstruction for Reduction of Metal Artifacts in Computed Tomography", PhD Thesis, University of Leuven, 2001.
W.A. Kalender, et al, "Reduction of CT Artifacts caused by Metallic Implants", Radiology, pp. 576-577, Aug. 1987.
R.M. Lewitt, et al, Image Reconstruction from Projections : III : Projection Completion Methods (theory), Optik 50 (1978) No. 3, pp. 189-204.

* cited by examiner

*Primary Examiner*—David V. Bruce
*Assistant Examiner*—Hoon Song
(74) *Attorney, Agent, or Firm*—Fletcher Yoder

(57) ABSTRACT

A method and computer-readable medium for reducing artifacts in image data generated by a computed tomography system is provided. The artifacts are due to the presence of a high density object in a subject of interest. The method comprises receiving measured sinogram data from the computed tomography system. The sinogram data is representative of sinogram elements. The measured sinogram data is reconstructed to generate initial reconstructed image data. Then corrected sinogram data is generated using the measured sinogram data. The corrected sinogram data is iteratively reconstructed to generate an improved reconstructed image data based on a weight measure derived from the measured sinogram data.

26 Claims, 4 Drawing Sheets

METHOD AND APPARATUS FOR REDUCTION OF ARTIFACTS IN COMPUTED TOMOGRAPHY IMAGES

BACKGROUND OF THE INVENTION

The present invention generally relates to the field of image reconstruction in computed tomography (CT) systems and more particularly to a method and apparatus for reducing artifacts in image data generated by computed tomography systems.

CT scanners operate by projecting fan shaped or cone shaped X-ray beams through an object. The X-ray beams are generated by an X-ray source, and are generally collimated prior to passing through the object being scanned. The attenuated beams are then detected by a set of detector elements. The detector elements produce a signal based on the intensity of the attenuated X-ray beams, and the signals are processed to produce projections. By using reconstruction techniques, such as filtered backprojection, useful images are formed from these projections.

A computer is able to process and reconstruct images of the portions of the object responsible for the radiation attenuation. As will be appreciated by those skilled in the art, these images are computed by processing a series of angularly displaced projection images. This data is then reconstructed to produce the reconstructed image, which is typically displayed on a cathode ray tube, and may be printed or reproduced on film.

As CT scanners are developed with larger and larger detectors, they begin to encounter problems with artifacts in the reconstructed image that arise due to the cone angle of the scanner. An increase in the cone angle beyond a certain limit can result in a degradation of the image quality produced by the scanner. Another particular problem with reconstructed images in CT systems are artifacts caused by the presence of high density objects, for example, metal objects in a subject. The presence of such high density objects in a subject causes relatively high attenuation of the X-ray beams as they propagate through the subject, thereby resulting in a reconstructed image with artifacts. The artifacts are due to one or more effects such as beam hardening, measurement noise, scatter, partial volume effect, aliasing, object motion and photon starvation.

Many techniques have been employed to reduce artifacts in image reconstructions. Some of these techniques include pre-processing of the sinogram data, modifying the reconstruction algorithm to reduce artifacts, or through post-processing of the reconstructed image. Pre-processing of the sinogram data comprises correcting for physical effects such as beam hardening, partial volume and scatter, or using adaptive filtering or projection completion techniques. Modifying the reconstruction algorithm comprises ignoring measurements through the high density objects, using special image basis functions, incorporating the physics of the acquisition in the reconstructed algorithm, using lower weights for corrupted measurements or including prior information. Post-processing the reconstructed image typically comprises removing artifact streaks using pattern recognition or by applying reformats to avoid and average out the artifacts.

A disadvantage of the above techniques is that they result in either only a partial reduction of artifacts, introduce new artifacts, have a high computation time or result in the formation of blurred images. Therefore, there exists a need in the art for an improved technique for generating image data with reduced artifacts.

BRIEF DESCRIPTION OF THE INVENTION

In one embodiment, a method and computer-readable for reducing artifacts in image data generated by a computed tomography system is provided. The artifacts are due to the presence of a high density object in a subject of interest. The method comprises receiving measured sinogram data from the computed tomography system. The sinogram data is representative of a plurality of sinogram elements. The measured sinogram data is reconstructed to generate initial reconstructed image data. Then corrected sinogram data is generated using the measured sinogram data. The corrected sinogram data is iteratively reconstructed to generate an improved reconstructed image data based on a weight measure derived from the measured sinogram data.

In another embodiment, a computed tomography system for reducing artifacts in image data is provided. The artifacts are due to the presence of a high density object in a subject of interest. The system comprises an X-ray source, a detector and a processor. The X-ray source is configured to project an X-ray beam from a plurality of positions through the subject of interest. The detector is configured to produce a plurality of electrical signals corresponding to the X-ray beam. The processor is configured to process the electrical signals to generate measured sinogram data, the sinogram data being representative of a plurality of sinogram elements. Further, the processor is configured to reconstruct the measured sinogram data to generate initial reconstructed image data, generate corrected sinogram data using the measured sinogram data and iteratively reconstruct the corrected sinogram data to generate an improved reconstructed image data based on a weight measure derived from the measured sinogram data.

BRIEF DESCRIPTION OF THE DRAWINGS

The foregoing and other advantages and features of the invention will become apparent upon reading the following detailed description and upon reference to the drawings in which.

DETAILED DESCRIPTION OF SPECIFIC EMBODIMENTS

Figure 1:
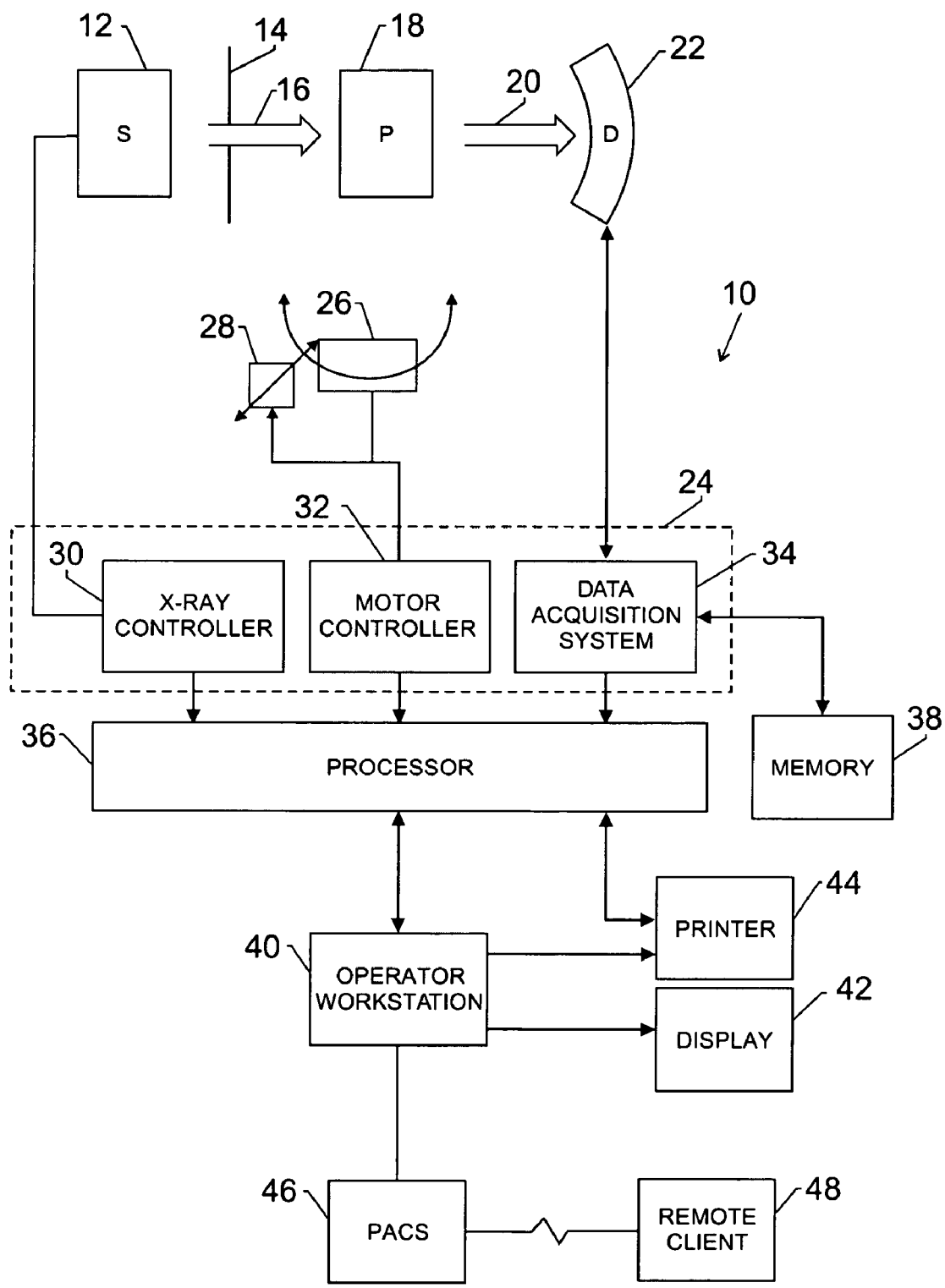
FIG. 1 is a diagrammatical view of an exemplary imaging system in the form of a CT imaging system for use in producing processed images according to one embodiment of the present technique.

FIG. 1 illustrates diagrammatically an imaging system 10 for acquiring and processing image data. In the illustrated embodiment, system 10 is a computed tomography (CT) system designed both to acquire original image data, and to process the image data for display and analysis in accordance with the present technique. In the embodiment illustrated in FIG. 1, imaging system 10 includes a source of X-ray radiation 12 positioned adjacent to a collimator 14. In this exemplary embodiment, the source of X-ray radiation source 12 is typically an X-ray tube.

Collimator 14 permits a stream of radiation 16 to pass into a region in which an object, for example, a subject of interest 18 is positioned. A portion of the radiation 20 passes through or around the subject and impacts a detector array, represented generally at reference numeral 22. Detector elements of the array produce electrical signals that represent the intensity of the incident X-ray beam. These signals are acquired and processed to reconstruct images of the features within the subject 18.

Source 12 is controlled by a system controller 24, which furnishes both power, and control signals for CT examination sequences. Moreover, detector 22 is coupled to the system controller 24, which commands acquisition of the signals generated in the detector 22. The system controller 24 may also execute various signal processing and filtration functions, such as for initial adjustment of dynamic ranges, interleaving of digital image data, and so forth. In general, system controller 24 commands operation of the imaging system to execute examination protocols and to process acquired data. In the present context, system controller 24 also includes signal processing circuitry, typically based upon a general purpose or application-specific digital computer, associated memory circuitry for storing programs and routines executed by the computer, as well as configuration parameters and image data, interface circuits, and so forth.

In the embodiment illustrated in FIG. 1, system controller 24 is coupled to a rotational subsystem 26 and a linear positioning subsystem 28. The rotational subsystem 26 enables the X-ray source 12, collimator 14 and the detector 22 to be rotated one or multiple turns around the subject 18. It should be noted that the rotational subsystem 26 might include a gantry. Thus, the system controller 24 may be utilized to operate the gantry. The linear positioning subsystem 28 enables the subject 18, or more specifically a table, to be displaced linearly. Thus, the table may be linearly moved within the gantry to generate images of particular areas of the subject 18.

Additionally, as will be appreciated by those skilled in the art, the source of radiation may be controlled by an X-ray controller 30 disposed within the system controller 24. Particularly, the X-ray controller 30 is configured to provide power and timing signals to the X-ray source 12. A motor controller 32 may be utilized to control the movement of the rotational subsystem 26 and the linear positioning subsystem 28.

Further, the system controller 24 is also illustrated comprising a data acquisition system 34. In this exemplary embodiment, the detector 22 is coupled to the system controller 24, and more particularly to the data acquisition system 34. The data acquisition system 34 receives data collected by readout electronics of the detector 22. The data acquisition system 34 typically receives sampled analog signals from the detector 22 and converts the data to digital signals for subsequent processing by a processor 36.

The processor 36 is typically coupled to the system controller 24. The data collected by the data acquisition system 34 may be transmitted to the processor 36 and moreover, to a memory 38. It should be understood that any type of memory to store a large amount of data might be utilized by such an exemplary system 10. Moreover, the memory 38 may be located at this acquisition system or may include remote components for storing data, processing parameters, and routines described below. Also the processor 36 is configured to receive commands and scanning parameters from an operator via an operator workstation 40 typically equipped with a keyboard and other input devices. An operator may control the system 10 via the input devices. Thus, the operator may observe the reconstructed image and other data relevant to the system from processor 36, initiate imaging, and so forth.

A display 42 coupled to the operator workstation 40 may be utilized to observe the reconstructed image and to control imaging. Additionally, the scanned image may also be printed by a printer 44 which may be coupled to the operator workstation 40. The display 42 and printer 44 may also be connected to the processor 36, either directly or via the operator workstation 40. Further, the operator workstation 40 may also be coupled to a picture archiving and communications system (PACS) 46. It should be noted that PACS 46 might be coupled to a remote system 48, radiology department information system (RIS), hospital information system (HIS) or to an internal or external network, so that others at different locations may gain access to the image and to the image data.

It should be further noted that the processor 36 and operator workstation 40 may be coupled to other output devices, which may include standard, or special purpose computer monitors and associated processing circuitry. One or more operator workstations 40 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

Figure 2:
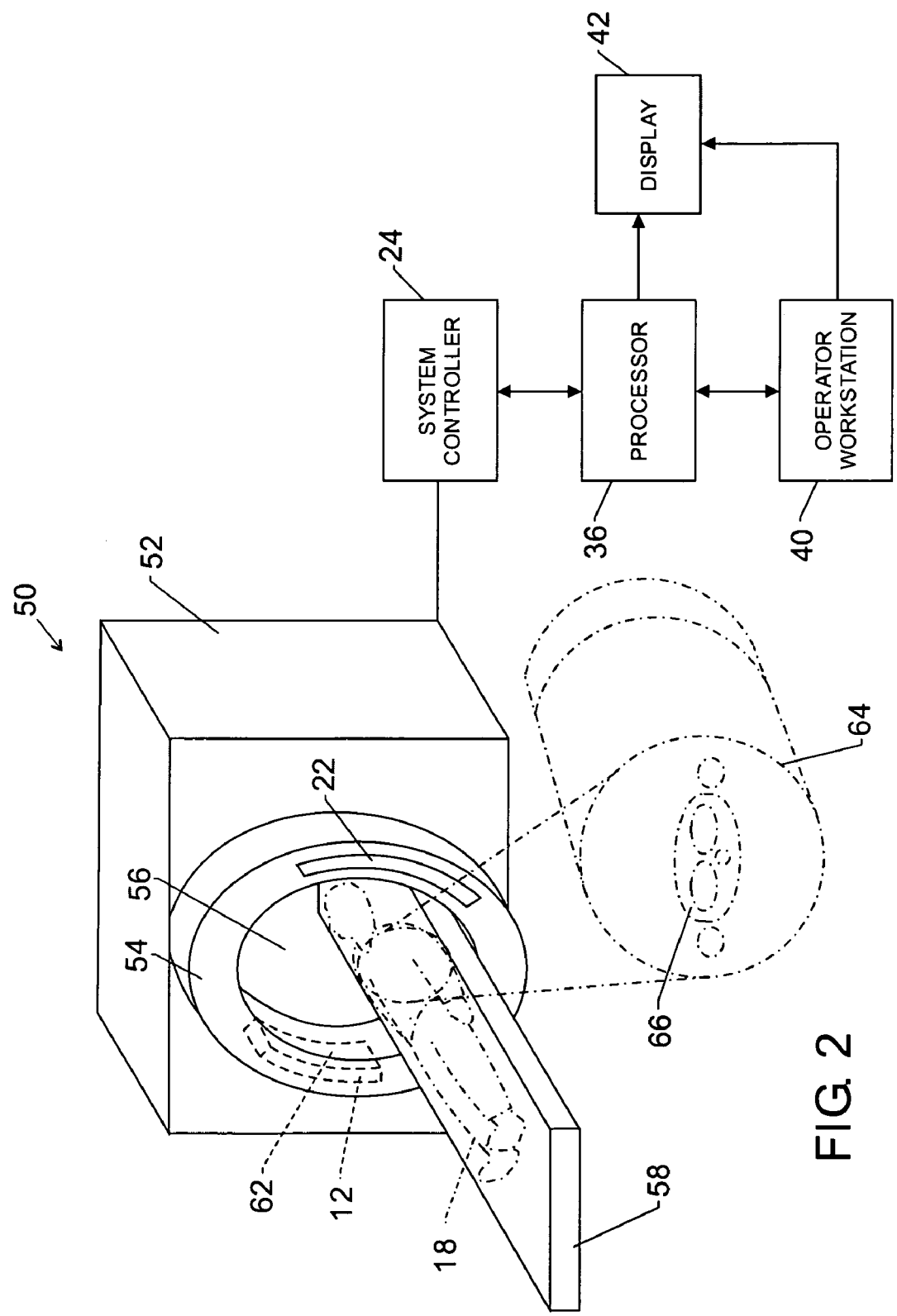
FIG. 2 is another diagrammatical view of a physical implementation of the CT system of FIG. 1.

Referring generally to FIG. 2, an exemplary imaging system utilized in a present embodiment may be a CT scanning system 50. The CT scanning system 50 is typically a multi-slice detector CT (MDCT) system that offers a wide array of axial coverage, high gantry rotational speed, and high spatial resolution. The CT scanning system 50 is illustrated with a frame 52 and a gantry 54 that has an aperture 56. The aperture 56 may typically be 50 cm in diameter. Further, a table 58 is illustrated positioned in the aperture 56 of the frame 52 and the gantry 54. Additionally, the table 58 is configured to be displaced linearly by the linear positioning subsystem 28 (see FIG. 1). The gantry 54 is illustrated with the source of radiation 12, typically an X-ray tube that emits X-ray radiation from a focal point 62. In typical operation, X-ray source 12 projects an X-ray beam from the focal point 62 toward detector array 22. The detector 22 is generally formed by a plurality of detector elements, which sense the X-ray beams that pass through and around a subject of interest. Each detector element produces an electrical signal that represents the intensity of the X-ray beam at the position of the element at the time the beam strikes the detector. Furthermore, the gantry 54 is rotated around the subject of interest so that a plurality of radiographic views may be collected by the processor 36. Thus, an image or slice is computed which may incorporate, in certain modes, less or more than 360 degrees of projection data, to formulate an image. The image is collimated to desired dimensions, using either lead shutters in front of the X-ray source 12 and different detector apertures. The collimator 14 (see FIG. 1) typically defines the size and shape of the X-ray beam that emerges from the X-ray source 12. Thus, as the X-ray source 12 and the detector 22 rotate, the detector 22 collects data of the attenuated X-ray beams.

Data collected from the detector 22 then undergoes preprocessing and calibration to condition the data to represent the line integrals of the attenuation coefficients of the scanned objects. The processed data, commonly called projections, are then filtered and backprojected to formulate an image of the scanned area. As mentioned above, the processor 36 is typically used to control the entire CT system 10. The main processor that controls the operation of the system may be adapted to control features enabled by the system controller 24. Further, the operator workstation 40 is coupled to the processor 36 as well as to a display, so that the reconstructed image may be viewed.

Alternatively, some or all of the processing described herein may be performed remotely by additional computing resources based upon raw or partially processed image data. In accordance with present technique, the processor is configured to generate improved reconstructed image data using the technique as described in subsequent paragraphs.

While in the present discussion reference is made to a CT scanning system in which a source and detector rotate on a gantry arrangement, it should be borne in mind that the present technique is not limited to data collected on any particular type of scanner. For example, the technique may be applied to data collected via a scanner in which an X-ray source and a detector are effectively stationary and an object is rotated, or in which the detector is stationary but an X-ray source rotates. Further, the data could originate in a scanner in which both the X-ray source and detector are stationary, as where the X-ray source is distributed and can generate X-rays at different locations. Similarly, while generally circular scan geometries are discussed, other geometries may be envisioned as well. Once reconstructed, the image produced by the system of FIGS. 1 and 2 reveals internal features of an object. As illustrated generally in FIG. 2, the image 64 may be displayed to show these features, such as indicated at reference numeral 66 in FIG. 2. Further, the present technique could apply to three-dimensional or cone beam acquisitions as well as to two-dimensional acquisitions.

Figure 3:
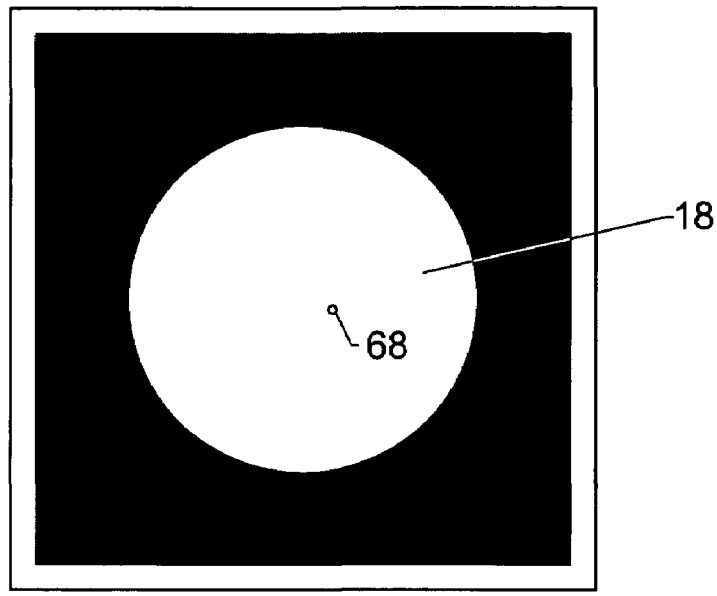
FIG. 3 is an illustration of a high density object in a subject in accordance with the present technique.

FIG. 3 is an illustration of a high density object in a subject of interest in accordance with the present technique. As shown in FIG. 3, reference numeral 18 represents the subject of interest, for example a patient and reference numeral 68 represents a high density object, for example a metal object. The presence of such high density objects in the subject 18 causes the appearance of artifacts in the reconstructed image. High density objects could include for example dental fillings, prosthetic devices or surgical clips in the subject of interest 18. That is, the presence of high density objects causes strong attenuation of the X-ray beams as they are projected through the subject, thereby resulting in a reconstructed image with metal streak artifacts, that are generally visible as bright and dark streaks or bands in the reconstructed image.

Figure 4:
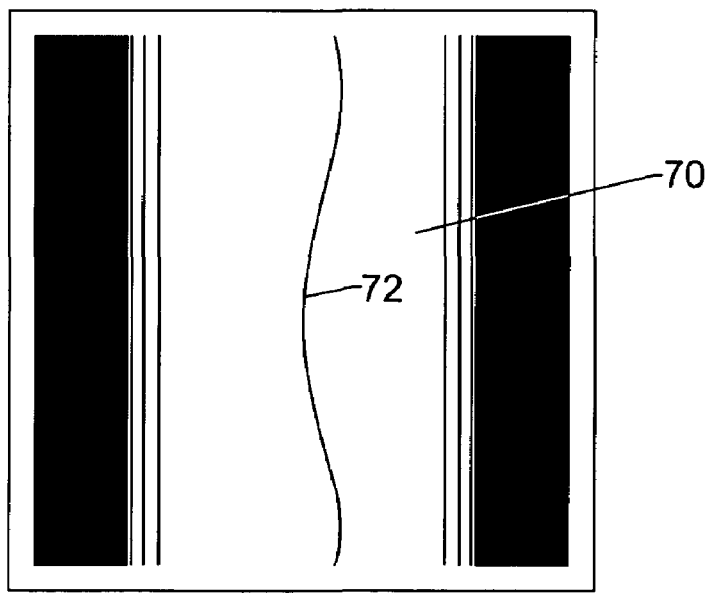
FIG. 4 is a representation of data collected by the data acquisition system of FIG. 1, presented as a sinogram, in accordance with the present technique.

FIG. 4 is a representation of the data collected by the data acquisition system 34 of FIG. 1 presented as a sinogram, 70, in accordance with the present technique. As will be appreciated by those skilled in the art, a sinogram is a collection of output data from the detector array 22 resulting from radiation traversing the subject of interest 18 at a given source position. The output data from each source and detector position or view corresponds to a row of projection data in the sinogram 70. As used herein, the term projection data is sometimes referred to as measured sinogram data. The measured sinogram data is representative of a plurality of sinogram elements. Thus, as illustrated in FIG. 4, each row of the sinogram 70 constitutes a projection view that is indicative of the attenuation information for a distinct view angle, for given source and detector positions, with respect to the subject 18. As described in greater detail below, these projection views are then processed to generate reconstructed image data (cross-sectional images) of the subject 18 at the given position.

Referring again to FIG. 4, reference numeral 72 indicates measured sinogram data affected by the presence of the high density object 68 in a plurality of view angles. As will be appreciated by those skilled in the art, except for objects lying at the center of the CT system 10, all objects will appear in the sinogram 70 as a sine-like wave, whose position corresponds to their location in the subject of interest. That is, the location of particular data resulting from attenuation by the presence of a high density object appears as a distinguishable sinusoidal trace 72. The high attenuation and the associated physical side effects cause errors in the measured sinogram data and this results in the presence of streaks in the reconstructed image data as described in greater detail below.

Figure 5:
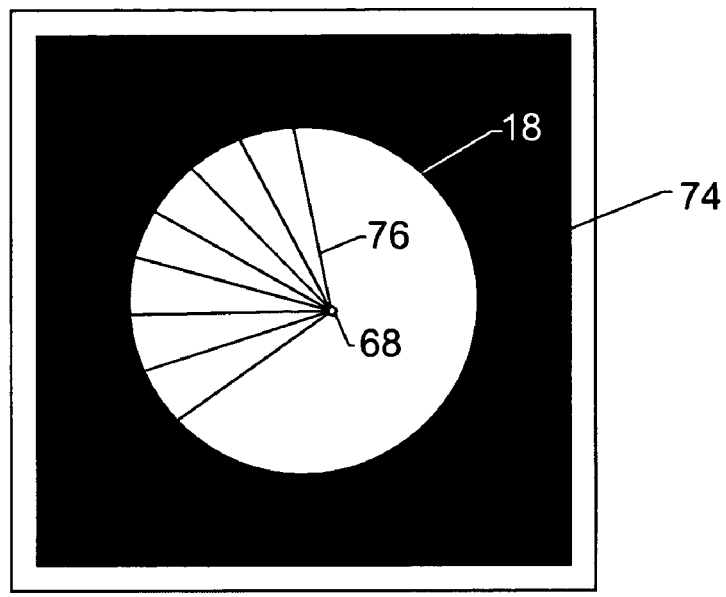
FIG. 5 is an illustration of reconstructed image data in accordance with the present technique.

FIG. 5 is an illustration of reconstructed image data 74 in accordance with the present technique. The measured sinogram data, comprising the sinogram 70 as illustrated in FIG. 4 is reconstructed to generate the reconstructed image data. Various image reconstruction techniques are available and may be used in the present technique to generate initial reconstructed image data. In a present embodiment, a filtered backprojection technique is used to generate the initial reconstructed image data. As will be appreciated by those skilled in the art, a filtered backprojection technique generally comprises the steps of weighting, filtering and backprojection of data of the measured sinogram data. The weighting of the sinogram data is performed with a point-by-point multiplication by a pre-calculated 2D array. The filtering or convolution step filters the sinogram data to decorrelate them and is carried out as a series of one-dimensional convolutions. In the backprojection step, the measured sinogram data is added to all picture elements in an image along the projection lines of the original projection views.

Referring again to FIG. 5, reference numeral 68 represents the high density object in the initial reconstructed image data. The presence of the high density object 68 in the subject 18 causes artifacts to appear in the initial reconstructed image data. As described above, the high density object comprises metal objects such as, for example, dental fillings, prosthetic devices or surgical clips in the subject 18. These high density objects strongly attenuate all or part of the X-ray beam incident on the detector 22. The strong attenuation introduces or enhances a number of effects such as noise, beam hardening, scatter, partial volume and aliasing causing the attenuation measurements to be incorrect. Errors in the attenuation measurements result in artifacts that appear as streaks or lines through the reconstructed image data as illustrated by the reference numeral 76.

Figure 6:
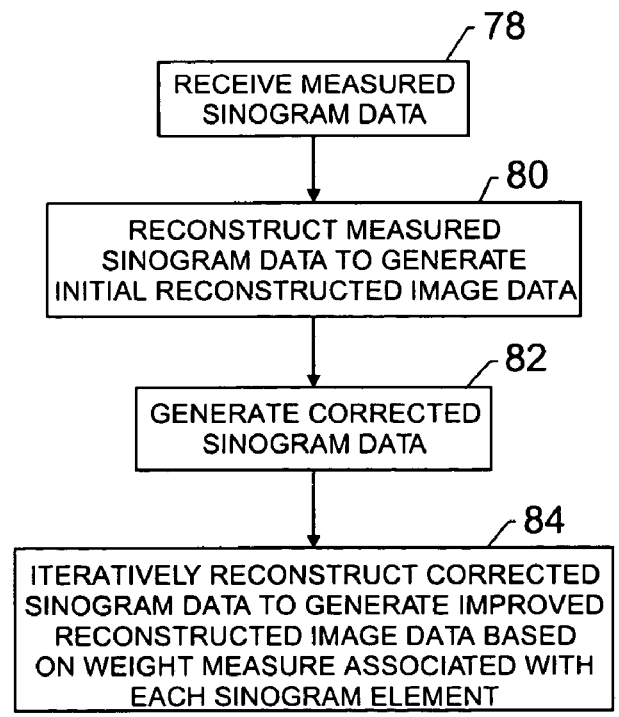
FIG. 6 is a flowchart illustrating the steps performed for reducing artifacts in image data generated by the CT system of FIG. 1 in accordance with the present technique.

FIG. 6 is a flowchart illustrating the steps performed for reducing artifacts in image data generated by the CT system of FIG. 1 in accordance with the present technique. In step 78, measured sinogram data from the computed tomography system is received. As described above, the sinogram data is representative of a plurality of sinogram elements. In step 80, the measured sinogram data is reconstructed to generate initial reconstructed image data. As described above, the initial reconstructed image data is generated using the filtered back projection technique in accordance with the present technique. In step 82, corrected sinogram data is generated using the measured sinogram data.

Various techniques are available and may be used by the present technique to generate corrected sinogram data. In a present embodiment, the projection completion technique is used to generate the corrected sinogram data. As will be appreciated by one skilled in the art, a typical projection completion technique generally comprises the steps of segmenting high density objects, for example, metal objects, from the initial reconstructed image data using a pre-defined threshold value and reprojecting an image comprising the high-density object. Parts of the measured sinogram data corresponding to non-zero values are defined as missing data. The missing values are replaced by linear interpolation on a view-by-view basis.

In accordance with the present technique, generating corrected sinogram data comprises identifying a trace of the high density object in the measured sinogram data and correcting the measured sinogram data in the trace of the high density object. In accordance with one embodiment of the present technique, identifying a trace of the high density object comprises segmenting the high density object from the initial reconstructed image data and reprojecting the segmented high density object from the initial reconstructed image data to generate reprojected sinogram data. The trace of the segmented high density object is then identified based on the reprojected sinogram data. In a specific embodiment, identifying the trace of the segmented high density object comprises comparing each sinogram element in the reprojected sinogram data to a pre-defined threshold value. In an alternate embodiment, identifying the trace of the high density object comprises comparing each sinogram element in the measured sinogram data to the pre-defined threshold value. The pre-defined threshold value is selected based upon a number of factors such as size, shape and density of the subject, and size, shape and density of the high-density objects. In yet another embodiment, identifying the trace of the high density object comprises assigning a reliability measure to each sinogram element in the measured sinogram data. As used herein, the reliability measure generally corresponds to the degree of allowable adjustment to the sinogram elements in the measured sinogram data.

Referring again to step 82 correcting the measured sinogram data in the trace of the high density object is performed using an interpolation technique. In this technique, the trace of the high density object in the measured sinogram data is replaced by interpolated data. In an alternate embodiment, correcting the measured sinogram data may be performed using techniques such as consistent completion techniques, spline based completion techniques, iterative correction techniques and non iterative correction techniques. One of ordinary skill in the art will recognize that the above listing of techniques is for illustrative purposes and is not meant to limit the use of other types of techniques by the CT system 10 for correcting the sinogram data.

In step 84, the corrected sinogram data is iteratively reconstructed to generate improved reconstructed image data based on a weight measure associated with each sinogram element. Various iterative reconstruction techniques are available and may be used in the present technique to iteratively reconstruct the corrected sinogram data. In a present embodiment, a maximum likelihood (ML) or a maximum a posteriori (MAP) technique is used.

As used herein, the weight measure generally corresponds to a function that is inversely proportional to the variance or to the standard deviation of the signal associated with each sinogram element. In accordance with one embodiment of the present technique, the weight measure is derived based on the measured sinogram data. In an alternate embodiment, the weight measure is derived based on a relative position of each sinogram element with respect to the trace of the high density object. In yet another alternate embodiment, the weight measure is derived based on simulated sinogram data. As will be appreciated by those skilled in the art, the sinogram elements in the trace of the high density object are less reliable and hence assigned a lower weight measure.

The embodiments described above have several advantages, including a reduction of the appearance of new streaks in the reconstructed image and removal of blurring effects in the reconstructed image. The present technique achieves the above advantages by iteratively reconstructing the corrected sinogram data to generate an improved reconstructed image data based on a weight measure derived from the measured sinogram data.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method for reducing artifacts in image data generated by a computed tomography system, the artifacts being due to the presence of a high-density object in a subject of interest, the method comprising:
   receiving measured sinogram data from the computed tomography system, the sinogram data representative of a plurality of sinogram elements;
   reconstructing the measured sinogram data to generate initial reconstructed image data;
   generating corrected sinogram data using the measured sinogram data; and
   iteratively reconstructing the corrected sinogram data to generate improved reconstructed image data based on a weight measure associated with each sinogram element, wherein the weight measure corresponds to a function that is inversely proportional to a variance or to a standard deviation of a signal associated with each sinogram element in the measured sinogram data, throughout the iterative reconstruction.

2. The method of claim 1, wherein generating corrected sinogram data using the measured sinogram data comprises using a projection completion technique.

3. The method of claim 2, wherein generating corrected sinogram data further comprises identifying a trace of the high density object in the measured sinogram data; and correcting the measured sinogram data in the trace of the high density object.

4. The method of claim 3, wherein identifying a trace of the high density object comprises:
   segmenting the high density object from the initial reconstructed image data;
   reprojecting the segmented high density object from the initial reconstructed image data to generate reprojected sinogram data; and
   identifying a trace of the high-density object based on the reprojected sinogram data.

5. The method of claim 3, wherein identifying the trace of the high-density object comprises comparing each sinogram element in the measured sinogram data to a pre-defined threshold value.

6. The method of claim 3, wherein identifying the trace of the high-density object comprises assigning a reliability measure to each sinogram element in the measured sinogram data.

7. The method of claim 3, wherein correcting the measured sinogram data is performed using an interpolation technique.

8. The method of claim 3, wherein correcting the measured sinogram data is performed using techniques selected from the group consisting of consistent completion techniques, spline based completion techniques, iterative correction techniques and non iterative correction techniques.

9. The method of claim 1, wherein the weight measure is derived based on a relative position of each sinogram element with respect to the trace of the high-density object.

10. The method of claim 1, wherein the weight measure is derived based on simulated sinogram data.

11. The method of claim 1, wherein the initial reconstructed image data is generated using a filtered back projection technique.

12. The method of claim 1, wherein iteratively reconstructing the corrected sinogram data to generate improved reconstructed image data is performed using techniques selected from the group consisting of maximum likelihood (ML) techniques and maximum a posteriori (MAP) techniques.

13. A method for reducing artifacts in image data generated by a computed tomography system, the artifacts being due to the presence of a high density object in a subject of interest, the method comprising:
   receiving measured sinogram data from the computed tomography system, the sinogram data representative of a plurality of sinogram elements;
   reconstructing the measured sinogram data to generate initial reconstructed image data;
   generating corrected sinogram data using the measured sinogram data;
   assigning a weight measure to each sinogram element in the corrected sinogram data, wherein the weight measure corresponds to a function that is inversely proportional to a variance or to a standard deviation of a signal associated with each sinogram element in the measured sinogram data; and
   iteratively reconstructing the corrected sinogram data to generate improved reconstructed image data based on the weight measure, throughout the iterative reconstruction.

14. The method of claim 13, wherein generating corrected sinogram data using the measured sinogram data comprises using a projection completion technique.

15. The method of claim 14, wherein generating corrected sinogram data further comprises identifying a trace of the high density object in the measured sinogram data; and correcting the measured sinogram data in the trace of the high density object.

16. The method of claim 15, wherein identifying a trace of the high density object comprises:
   segmenting the high density object from the initial reconstructed image data;
   reprojecting the segmented high density object from the initial reconstructed image data to generate reprojected sinogram data; and
   identifying a trace of the high-density object based on the reprojected sinogram data.

17. The method of claim 15, wherein identifying the trace of the high-density object comprises comparing each sinogram element in the measured sinogram data to a predefined threshold value.

18. The method of claim 15, wherein identifying the trace of the high-density object comprises assigning a reliability measure to each sinogram element in the measured sinogram data.

19. The method of claim 15, wherein correcting the measured sinogram data is performed using an interpolation technique.

20. The method of claim 15, wherein correcting the measured sinogram data is performed using techniques selected from the group consisting of consistent completion techniques, spline based completion techniques, iterative correction techniques and non iterative correction techniques.

21. The method of claim 13, wherein the initial reconstructed image data is generated using a filtered back projection technique.

22. The method of claim 13, wherein iteratively reconstructing the corrected sinogram data to generate improved reconstructed image data is performed using techniques selected from the group consisting of maximum likelihood (ML) techniques and maximum a posteriori (MAP) techniques.

23. A computed tomography system for reducing artifacts in image data, the artifacts being due to the presence of a high density object in a subject of interest, the system comprising:
   an X-ray source configured to project an X-ray beam from a plurality of positions through the subject of interest;
   a detector configured to produce a plurality of electrical signals corresponding to the X-ray beam; and
   a processor configured to process the electrical signals to generate measured sinogram data, the sinogram data representative of a plurality of sinogram elements, wherein the processor is further configured to reconstruct the measured sinogram data to generate initial reconstructed image data; generate corrected sinogram data using the measured sinogram data and iteratively reconstruct the corrected sinogram data to generate an improved reconstructed image data based on a weight measure associated with each sinogram element, wherein the weight measure corresponds to a function that is inversely proportional to a variance or to a standard deviation of a signal associated with each sinogram element in the measured sinogram data, throughout the iterative reconstruction.

24. At least one computer-readable medium storing computer instructions for instructing a computer system to reduce artifacts in image data generated by a computed tomography system, the artifacts being due to the presence of a high density object in a subject of interest, the computer instructions comprising:
   receiving measured sinogram data from the computed tomography system, the sinogram data representative of a plurality of sinogram elements;
   reconstructing the measured sinogram data to generate initial reconstructed image data;
   generating corrected sinogram data using the measured sinogram data; and
   iteratively reconstructing the corrected sinogram data to generate an improved reconstructed image data based on a weight measure associated with each sinogram element, wherein the weight measure corresponds to a function that is inversely proportional to a variance or to a standard deviation of a signal associated with each sinogram element in the measured sinogram data, throughout the iterative reconstruction.

25. At least one computer-readable medium storing computer instructions for instructing a computer system to reduce artifacts in image data generated by a computed tomography system, the artifacts being due to the presence of a high density object in a subject of interest, the computer instructions comprising:
- receiving measured sinogram data from the computed tomography system, the sinogram data representative of a plurality of sinogram elements;
- reconstructing the measured sinogram data to generate initial reconstructed image data;
- generating corrected sinogram data using the measured sinogram data;
- assigning a weight measure to each sinogram element in the corrected sinogram data, wherein the weight measure corresponds to a function that is inversely proportional to a variance or to a standard deviation of a signal associated with each sinogram element in the measured sinogram data; and
- iteratively reconstructing the corrected sinogram data to generate improved reconstructed image data based on the weight measure, throughout the iterative reconstruction.

26. A computed tomography system for reducing artifacts in image data, the artifacts being due to the presence of a high density object in a subject of interest, the system comprising:
- means for processing a plurality of electrical signals corresponding to an X-ray beam generated by the computed tomography system to generate measured sinogram data, the sinogram data representative of a plurality of sinogram elements, wherein the processing further comprises reconstructing the measured sinogram data to generate initial reconstructed image data; generate corrected sinogram using the measured sinogram data; and iteratively reconstructing the corrected sinogram data to generate an improved reconstructed image data based on a weight measure associated with each sinogram element, wherein the weight measure corresponds to a function that is inversely proportional to a variance or to a standard deviation of a signal associated with each sinogram element in the measured sinogram data, throughout the iterative reconstruction.

* * * * *